US00PP09545P

United States Patent [19]

Frazer

[11] Patent Number: Plant 9,545

[45] Date of Patent: May 7, 1996

[54] DIEFFENBACHIA PLANT NAMED TROPIC RAIN

[75] Inventor: Edwin J. Frazer, Kenmore, Australia

[73] Assignee: Twyford International Inc., Sebring, Fla.

[21] Appl. No.: 374,913

[22] Filed: Jan. 19, 1995

[51] Int. Cl.[6] ..... A01H 5/00

[52] U.S. Cl. ..... Plt./88.2

[58] Field of Search ..... Plt./88.2

*Primary Examiner*—James R. Feyrer
*Attorney, Agent, or Firm*—Foley & Lardner

[57] ABSTRACT

A Dieffenbachia plant named Tropic Rain particularly characterized by its long elliptical medium green leaves with contrasting white markings and its rosetted upright habit.

1 Drawing Sheet

The present invention comprises a new and distinct cultivar of Dieffenbachia, botanically known as *Dieffenbachia hybrida,* and referred to by the cultivar name Tropic Rain.

The new cultivar is a product of a planned breeding program carried out by the inentor Edwin J. Frazer in Brisbane, Australia. The new cultivar is a product of a cross made between presently unidentified parents of the following species:

Pollen parent: *Dieffenbachia amoena.*

Seed parent: *Dieffenbachia daguensis.*

The cultivar was discovered from the progeny of the stated cross by Edwin J. Frazer in Brisbane, Australia. Asexual propagation by tissue culture by the inventor in Brisbane, Australia increased the number of plants for evaluation and has demonstrated the stability of the combination of characteristics of Tropic Rain from generation to generation.

The following observations, measurements and values describe plants grown in Apopka, Fla. under greenhouse conditions which closely approximate those generally used in horticultural practice.

The following traits have been repeatedly observed to be characteristics which in combination particularly distinguish Tropic Rain from other cultivars.

1. The leaves are long, elliptical in shape, and distinctly tapered at the tip and base.

2. The leaves are medium green in color with abundant white markings of no specific and widely differing shapes which are normally elongated in directions parallel to the direction of the primary veins but not as extensive as the veins, and which may or may not overlap the primary veins.

3. The color pattern is visible from both sides of the leaf.

4. The growth habit is rosetted and upright.

All color references are measured against The Royal Horticultural Society Colour Chart. Colors are approximate as color depends on horticultural practices such as light level and fertilization rate, among others, without, however any variance in genotype.

The color photographic drawing comprises a top perspective view of a plant of Tropic Rain in a 21 cm pot approximately 40 weeks after planting a 12-week-old liner obtained by tissue culture and grown under appropriate growing conditions. Colors are as accurate as possible with color illustrations of this type.

Origin: Sterile seedling selected from a cross of:

*Pollen parent.—Dieffenbachia amoena.*

*Seed parent.—Dieffenbachia daguensis.*

Classification: *Dieffenbachia hybrida,* cv., Tropic Rain.

Propagation: Asexual propagation either by tissue culture or division.

Plant: In a 21 cm pot for a plant grown from a 12-week-old liner after 40 weeks under appropriate growing conditions, Tropic Rain reaches a height of approximately 23 cm to 29 cm from the soil surface to the junction of the petioles of the last two (2) unrolled leaves, and a width of approximately 76 cm to 80 cm.

*Stem.*—Growth pattern: The stem is erect in growth and approximately 3.2 cm to 3.5 cm in diameter five (5) cm above the soil surface. Internode distance is approximately 1.0 to 1.6 cm three (3) cm above the soil. Color: The stem is 146B-C, occasionally faintly mottled with 147C.

Petiole.—The following information is based on the 4th expanded leaf from the apex. Growth pattern: The petiole has fleshy edges, referred to as wings, extending from the midrib. The wings are approximately 9 mm to 15 mm wide one-half (½) the distance from the petiole base to the wing apex, and extend from the base of the petiole to the base of the leaf. The apex of the wings is unevenly emarginate. The petiole follows the stem axis but diverges from the axis approximately 8.3 cm to 10.7 cm from the base, forming a horizontal distance from the edge of the stem to the leaf base of approximately 2.2 cm. Dimensions: The petiole is straight from its base to the base of the leaf. The petiole is approximately 10 mm to 13 mm in diameter at the base of the leaf and approximately 14.7 cm to 16 cm in length from its base to the base of the leaf. Color: The petiole wings are darker and greener than, but closer to 137A. The midrib of the petiole is 146B.

*Leaf.*—Growth pattern: The leaf is elliptical with a acuminate apex and an attenuate to acute cuneate base. The margin is entire. The leaf is asymmetric with the side of the leaf unrolling first having less surface area than the side unrolling last. The leaf is oriented parallel to the stem axis at the time of full unrolling, changing to approximately 50 degrees above perpendicular to the stem axis as more leaves unroll above it. The midrib is straight over the length of the leaf. The leaf blade is convex between the primary veins. Dimensions: For the pot size and growing time indicated, the largest leaf is approximately 46.2 cm to 49.5 cm long and approximately 17.2 cm to 18 cm wide. An average-sized leaf is approximately 41 cm to 45.5 cm long and approximately 16 cm to 18 cm wide. The leaf is moderately thick, and the surface is glossy. Midrib: The midrib is thick and prominent. Primary veins: The primary veins are sunken into the upper surface and protrude from the underside. The primary veins are the same color as the surrounding tissue.

The upper surface of both mature and newly opened leaves is predominantly medium green but conatins patterns of individual markings of random shapes and somewhat varied sizes, occurring between the midribs to near the margins in essentially uniform density from base to apex of the leaves. The markings are of white color which interestingly contrasts with the green predominating the laminas. Such markings are normally somewhat elongated in the direction of the primary veins of the leaves, and may or may not overlap such veins, to form a characteristically unpredictable but fairly distinctive pattern of contrasting colors from among the widely varying plants of this market class. Color: Mature Leaf: Upper surface: Darker than, but closest to 137A with spots and blotches of 155A; midrib 137A with streaks of 155A. Lower surface: 137B with spots and blotches lighter than, but closest to 145D; midrib 146D. Newly Opened Leaf: Upper surface: Greener than, but closest to 137A with spots and blotches of 155A; midrib 146B with streaks of 155A. Lower Surface: 137C with spots and blotches lighter than, but closest to 150D; midrib 146D. Axillary Breaks: There are approximately 2 to 4 axillary breaks with at least one leaf expanded. Leaves show color by the first leaf and will have true color and pattern by the second leaf. Inflorescence: Typical of Dieffenbachia and does not have commercial significance.

*Roots.*—Thick white roots with fine laterals.

General observations: Tropic Rain has long elliptical medium green leaves distinctly tapered at the tip and base and marked with contrasting white spots and blotches. The habit is rosetted and upright. These combined characteristics make Tropic Rain a unique new cultivar.

It is claimed:

1. A new and distinct cultivar of Dieffenbachia plant named Tropic Rain, as illustrated and described.

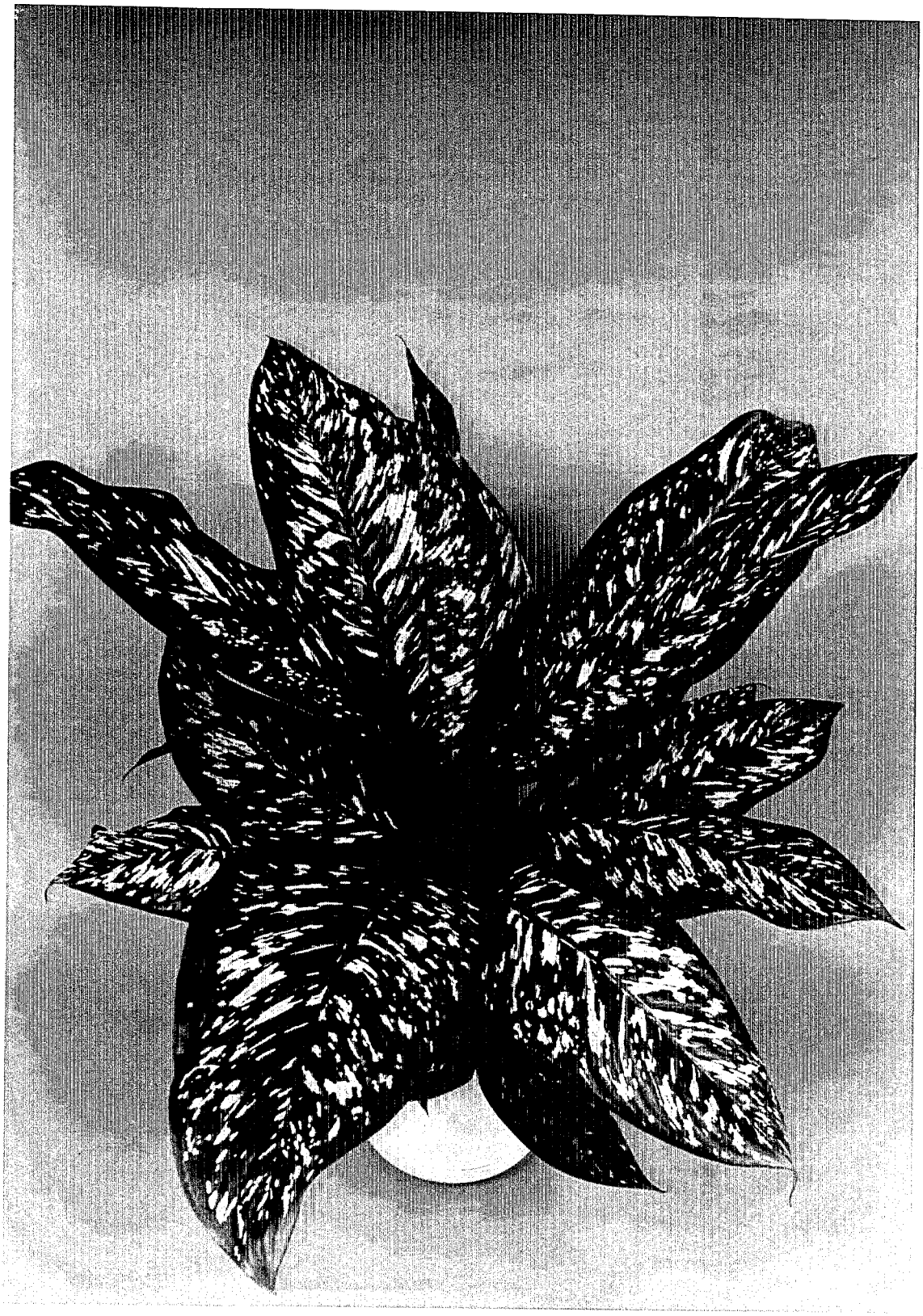

* * * * *